United States Patent
Maggiore et al.

(10) Patent No.: US 9,933,118 B2
(45) Date of Patent: Apr. 3, 2018

(54) SINGLE USE CONTAINER, SYSTEM AND METHOD FOR THE PREVENTION OF OVER-PRESSURIZATION

(71) Applicant: Sartorius Stedim Biotech GmbH, Goettingen (DE)

(72) Inventors: Frank Maggiore, Port Jefferson Station, NY (US); Cassandra Lorio, Selden, NY (US)

(73) Assignee: Sartorius Stedim Biotech GmbH (DE)

( * ) Notice: Subject to any disclaimer, the term of this patent is extended or adjusted under 35 U.S.C. 154(b) by 429 days.

(21) Appl. No.: 14/680,370

(22) Filed: Apr. 7, 2015

(65) Prior Publication Data

US 2016/0298810 A1    Oct. 13, 2016

(51) Int. Cl.
| | |
|---|---|
| *F17C 13/06* | (2006.01) |
| *C12M 1/00* | (2006.01) |
| *C12M 1/34* | (2006.01) |
| *F17C 13/04* | (2006.01) |

(52) U.S. Cl.
CPC .............. *F17C 13/06* (2013.01); *C12M 23/14* (2013.01); *C12M 23/26* (2013.01); *C12M 23/28* (2013.01); *C12M 41/40* (2013.01); *F17C 13/04* (2013.01); *F17C 2205/0323* (2013.01); *F17C 2205/0341* (2013.01); *F17C 2209/22* (2013.01); *F17C 2260/021* (2013.01)

(58) Field of Classification Search
CPC .. F17C 13/04; F17C 13/06; F17C 2205/0323; F17C 2205/0332; F17C 2205/0341; C12M 23/14; C12M 23/28; C12M 41/40
See application file for complete search history.

(56) References Cited

U.S. PATENT DOCUMENTS

| | | | | |
|---|---|---|---|---|
| 4,235,347 A | * | 11/1980 | Cothier | G01R 1/04 137/68.11 |
| 5,673,934 A | * | 10/1997 | Saccone | B60R 21/264 222/3 |
| 2005/0087570 A1 | * | 4/2005 | Jackman | B65D 83/0005 222/541.4 |
| 2011/0005984 A1 | * | 1/2011 | Boettcher | A61M 1/3621 210/137 |
| 2011/0207170 A1 | | 8/2011 | Niazi | |
| 2014/0024108 A1 | | 1/2014 | Hojsgaard | |

FOREIGN PATENT DOCUMENTS

CN         201265006 Y         7/2009

OTHER PUBLICATIONS

Extended European Search Report dated August 12, 2016.

* cited by examiner

*Primary Examiner* — Robert Clemente
(74) *Attorney, Agent, or Firm* — Gerald E. Hespos; Michael J. Porco; Matthew T. Hespos

(57) ABSTRACT

A single-use container for the prevention of over-pressurization is provided. The single-use container has an enclosure for a fluid and an over-pressurization relief device fluidly connected to the enclosure. The over-pressurization relief device is configured to relieve pressure from the enclosure when a pressure of the fluid within the enclosure exceeds a specified relief pressure. The specified relief pressure is set to be lower than the burst pressure of the enclosure. The over-pressurization relief device is connectable to a controlled pathway for relieving the fluid from the enclosure in a controlled manner.

25 Claims, 11 Drawing Sheets

SINGLE USE CONTAINER, SYSTEM AND METHOD FOR THE PREVENTION OF OVER-PRESSURIZATION

BACKGROUND

1. Field of the Invention

The application relates to a single-use container comprising an over-pressurization relief device, as well as a system provided therewith and a method to prevent over-pressurization.

2. Description of the Related Art

A single-use container is a disposable container, i.e. a container that is discarded after being used. A single-use container may be made of plastic, a synthetic material that can be molded into shape while soft and then set into a rigid or deformable form. Single-use containers are widely used in e.g. the field of bioprocessing, because they are advantageous in terms of cost and flexibility with respect to conventional stainless steel containers. Furthermore, a single-use system is easily sterilizable and helps reduce the risk of contaminations because of its disposability.

However, another decisive factor in the choice of the technology to be employed (i.e. single-use container or steel container) is the safety of the operations. In case of an event of over-pressurization, a breach in the container may ensue, leading to container leakage and loss of sterility. In particular, if biohazardous materials are used, operators may be exposed to dangerous substances.

There are multiple situations where fluid is entering into a container as an input and, if the introduction of the fluid is not properly regulated and/or vented, the pressure of the fluid can lead to the container exceeding the burst pressure. These situations of over-pressurization can include malfunctioning of a primary vent filter due to the presence of condensate, clamping the primary vent filter prior to a fluid addition to the container, over-pressurization due to an incorrect value and/or a faulty regulator of the fluid, pump speed input too high, incorrect integrity testing parameters for the container, and/or some other input without proper regulation, monitoring, and/or venting in place.

In order to protect a stainless steel container from an over-pressurization event, a rupture disc is commonly used. A rupture disc comprises a membrane that fails at a predetermined pressure and is usually made of metal.

US 2011/0005984 discloses a presterilizable filtration system to be disposed of after a single use. The recirculation tank in the system is provided with a safety valve to protect the tank from mechanical destruction by inadmissible excess pressure.

A safety valve may fail to operate and/or not be able to relieve pressure quickly enough. There is therefore a need for a single-use container in which contents can be efficiently relieved in a controlled manner prior to reaching a condition of over-pressurization in the single-use container.

SUMMARY OF THE INVENTION

According to one aspect, a single-use container is provided. The single-use container comprises the following: an enclosure for a fluid and an over-pressurization relief device fluidly connected to the enclosure, wherein the over-pressurization relief device is configured to relieve pressure from the enclosure when a pressure of the fluid within the enclosure exceeds a specified relief pressure, wherein the specified relief pressure is set to be lower than the burst pressure of the single-use container, and wherein the over-pressurization relief device is connectable to a controlled pathway for relieving the fluid from the enclosure in a controlled manner.

According to another aspect, a system for the prevention of over-pressurization in a single-use container is provided. The system comprises the following: a single-use container according to the above aspect, and a controlled pathway connected to the over-pressurization relief device of the single-use container.

According to a further aspect, a method to prevent over-pressurization in a single-use container is provided. The method comprises the following: connecting an enclosure for a fluid with an over-pressurization relief device for relieving pressure from the enclosure when a pressure of the fluid within the enclosure exceeds a specified relief pressure, wherein the specified relief pressure is set to be lower than the burst pressure of the enclosure, and connecting a controlled pathway to the over-pressurization relief device for relieving the fluid from the enclosure in a controlled manner.

Details of exemplary embodiments are set forth below with reference to the exemplary drawings. Other features will be apparent from the description, the drawings, and from the claims.

DETAILED DESCRIPTION

In the following text, a detailed description of examples will be given with reference to the drawings. It should be understood that various modifications to the examples may be made. In particular, one or more elements of one example may be combined and used in other examples to form new examples.

Figure 1:
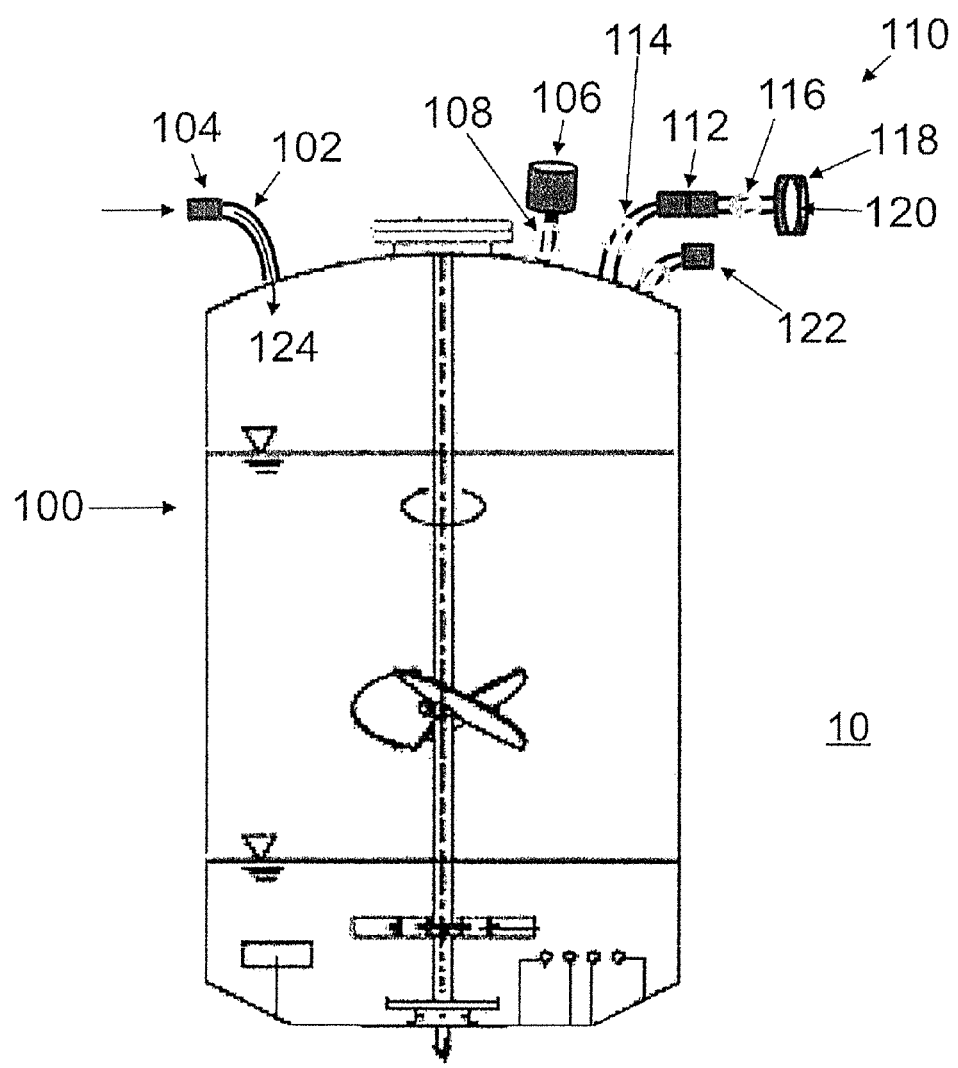
FIG. 1 shows an example of a single-use container.

FIG. 1 shows an example of a single-use container according to one embodiment.

A single-use container is a disposable container that is configured for a one-time use. After the single-use container has been used once, it has fulfilled its function and may be disposed of. Exemplarily, a single-use container is made of plastic, which may include but is not limited to polyamide, polycarbonate, polyethylene, polystyrene, polyethersulfone, polypropylene, polytetrafluoroethylene, polyvinyl chloride, cellulose acetate and/or ethyl vinyl acetate. In one example, the single-use container may be rigid, i.e. its shape may not be modified. In another example, the single-use container may have flexible walls, i.e. it may be capable of changing its shape without breaking.

Single-use containers may exemplarily be used for critical fluid handling applications in the biopharmaceutical and biomanufacturing industries. The use of a disposable container may include but is not limited to storage and product hold, mixing and/or cell cultivation. The single-use container 10 specifically is a sterilizable plastic disposable container that is adapted to contain or hold at least one fluid. It may be any one of a bioreactor bag, a mixing container, a 2D and a 3D bioprocessing bag.

Exemplarily, a single-use container may comprise an enclosure with a multilayer film structure, i.e. a superposition of thin layers of plastic materials that provides a secure barrier between the content of the enclosure (e.g. biohazardous material) and the external environment. At the same time, the disposability reduces the requirements for cleaning and sterilization, as well as the potential for contaminations. Furthermore, single-use containers may be exemplarily provided presterilized (e.g. by means of gamma irradiation and/or autoclaving). Single-use containers may thus provide an advantageous alternative to traditional glass and/or stainless steel systems.

The single-use container 10 shown in FIG. 1 may include an enclosure 100 and an over-pressurization relief device 120 fluidly connected to the enclosure 100. The enclosure 100 may contain a fluid, such as a gas, a liquid and/or a mixture thereof, wherein the fluid applies pressure to the walls of the enclosure. In an example, the enclosure 100 may be a Biostat® Cultibag® STR bioreactor bag. The over-pressurization relief device 120 is fluidly connected to the enclosure 100 in that a flow of fluid from the enclosure 100 to the over-pressurization relief device 120 is allowed. In one example, the over-pressurization relief device 120 may be integrated into the enclosure 100, e.g. the over-pressurization relief device 120 may be integrally attached to the enclosure 100 without connections comprising mechanical joints. The over-pressurization relief device 120 may be e.g. at least partly positioned within the multilayer structure of the enclosure 100 (e.g. a flange may be embedded and/or soldered to one or more layers of the multilayer structure). In another example, the over-pressurization relief device 120 may be externally connected to the enclosure 100. The over-pressurization relief device 120 may e.g. be located at an external container 118 that is connected to the enclosure 100 by means of an aseptic connection 112 such as a tubing connection comprising for example an external port, an internal port and a disposable connection device.

The over-pressurization relief device 120 may be a conditional barrier element, i.e. an element that acts as a barrier only under certain conditions. In other words, the over-pressurization relief device 120 may prevent or allow the transit of the fluid contained in the enclosure depending on a state of the single-use container 10. Exemplarily, a threshold pressure, or relief pressure, may be set to regulate the behavior of the over-pressurization relief device 120. When a pressure of the fluid within the enclosure 100 is below the specified (predetermined or predeterminable) relief pressure, the over-pressurization relief device 120 may act as a barrier, thereby keeping the fluid confined within the enclosure 100. When a pressure of the fluid within the enclosure 100 exceeds the specified relief pressure, the over-pressurization relief device 120 may instead let the fluid through, thereby relieving pressure from the enclosure 100.

Exemplarily, the specified relief pressure may be set to be lower than the burst pressure of the enclosure 100. The burst pressure of the enclosure 100 is the maximum pressure that the enclosure 100 can endure before its structural integrity is compromised. For example, exceeding the burst pressure may cause the enclosure 100 to burst, to tear and/or to break, thereby leaking the fluid contained within the enclosure 100. Therefore the liquid in the enclosure 100 should be prevented from reaching the burst pressure. When the over-pressurization relief device 120 is fluidly connected to the enclosure 100, crossing the specified relief pressure within the enclosure 100 triggers the pressure relief by the over-pressurization relief device 120, as explained above. Consequently, the pressure of the fluid within the enclosure 100 can never be higher than the specified relief pressure. By setting the specified relief pressure to be lower than the burst pressure, the over-pressurization relief device 120 prevents the liquid in the enclosure 100 from ever reaching the burst pressure.

Exemplarily, the over-pressurization relief device 120 may be connectable to a controlled pathway for relieving the fluid from the enclosure in a controlled manner. When the pressure of the fluid within the enclosure 100 is lower than the specified relief pressure, the over-pressurization relief device 120 functions as a barrier between the interior of the single-use container 10 and the external environment. When the threshold pressure is reached, the over-pressurization relief device 120 does not act as a barrier any longer and lets the fluid through. In other words, the over-pressurization relief device 120 may allow the fluid to move from within the enclosure 100 outwards. In an example, the over-pressurization relief device 120 may lead the fluid into an assembly that channels it towards a specified destination. Therefore the over-pressurization relief device 120 may provide a safe way to discharge fluid in excess with respect to a desired pressure in the enclosure 100, e.g. the specified relief pressure. Further details in this regard are provided with reference to FIGS. 6 and 7 below.

In an example, a pressure relief valve may be additionally utilized if the pressure within the enclosure 100 exceeds the capacity of the over-pressurization relief device 120 to relieve the pressure.

FIG. 1 shows an exemplary fluid connection between the enclosure 100 and the over-pressurization relief device 120, according to which the over-pressurization relief device 120 is located at the external container 118 and connected to an outlet tubing length from the enclosure 100 using an aseptic connection 112. The outlet tubing length from the enclosure 100 may for example comprise a clamp 114. A length of tubing with a clamp 116 may be positioned between the aseptic connection 112 and the external container 118. The ensemble of the tubing length and clamp 116, the external container 118 and the over-pressurization relief device 120 may form a relief assembly 110.

The aseptic connection 112 may be made using an aseptic connector such as an OPTA® connector and/or other physical aseptic connector, and/or may be achieved by thermowelding a tubing length of thermoweldable tubing to the relief assembly 110. In an example, the over-pressurization relief device 120 is configured such that it may be sterilized e.g. by a validated sterilization method, for example by gamma irradiation, chemical sterilant (such as with vaporized hydrogen peroxide, ethylene oxide, etc.), steam sterilization and/or autoclaving, prior to being connected to the enclosure 100. In another example, the over-pressurization relief device 120 may be sterilized along with the enclosure 100.

In an example, the single-use container 10 may comprise an input tubing length 102 with an aseptic connection 104 to receive an input of the fluid into the enclosure 100. In another example, the single-use container 10 may include a vent filter 106, which is e.g. a hydrophobic vent filter, and is associated with a vent filter clamp 108. In a further example, the single-use container may comprise an additional aseptic connection 122.

Exemplarily, a method to conduct operations with the single-use container 10 may comprise the following. The clamps 114 and 116 in the relief assembly 110 may be set to an open position and the vent filter clamp 108 may be set to a closed position.

A fluid may be introduced into the enclosure 100 through the input tubing length 102, thereby constituting an input pressure source 124 for the enclosure 100. The pressure of the fluid inside the enclosure 100 may then be increased by the input pressure source 124, since the vent filter clamp 108 is in the closed position and the over-pressurization relief device 120 acts initially as a barrier. When the specified relief pressure is reached, the over-pressurization relief device 120 may relieve pressure from the enclosure 100. Consequently the pressure increase stops and the burst pressure of the enclosure 100, which is higher than the specified relief pressure, is not reached. At this stage, the clamp 116 may be closed and the input pressure source 124 may be turned off, i.e. the introduction of fluid into the enclosure 100 may be stopped. A new relief assembly 110 may then be connected to the additional aseptic connection 122 available in the single-use container 10.

As explained above, the over-pressurization relief device 120 is a conditional barrier element that must have a dual behavior. Indeed, the over-pressurization relief device 120 should allow the single-use container to perform its functions in normal conditions of pressure (i.e. below the specified relief pressure) and hence provide a barrier to the fluid. On the other hand, when the specified relief pressure is reached, the over-pressurization relief device 120 should promptly switch to a non-obstructing state in which the fluid is let through. An exemplary candidate for the over-pressurization relief device 120 may be a sacrificial part configured to break under the specified relief pressure. For example, a thin layer of material, i.e. a film layer, may be used. A film layer may have a thickness in a range spanning from approximately some nanometers to approximately some millimeters, for example a thickness between about 1 μm and about 1000 μm. The film layer may consist of a single layer of film or a multi-layered film. In an example, the film layer may be made of plastic.

The film layer, when intact, may constitute a solid barrier that prevents the flow-through of the fluid. At the same time, the film layer may be configured to break at a breakage pressure corresponding to the specified relief pressure, thereby forming a gap that allows the transit of the fluid. In an example, the breakage pressure may coincide with the specified relief pressure. In another example, there may be means between the enclosure 100 and the over-pressurization relief device 120 to alter the specified relief pressure so that the breakage pressure may be different from the specified relief pressure.

The breakage pressure may be determined by e.g. properties of the material forming the layer. In another example, the film layer may undergo specific processing in order to be weakened in one or more positions and the weakening may set the breakage pressure. The processing is meant to assist the film layer to fail at the breakage pressure with consistency. In this example, the film layer may be stretched, perforated, chemically processed and/or physically processed.

The integrity of the film layer may be monitored by means of a sensor configured to trigger a signal in case the film layer breaks. Exemplarily, this signal may be a visual and/or an auditory alarm and/or any other indication method that may notify e.g. an operator of the breach. The sensor may be, but is not limited to, a pressure gauge, an indicator pressure gauge, a flow meter, a moisture sensor, a fluid sensor, and/or a pressure sensor.

Figure 2A:
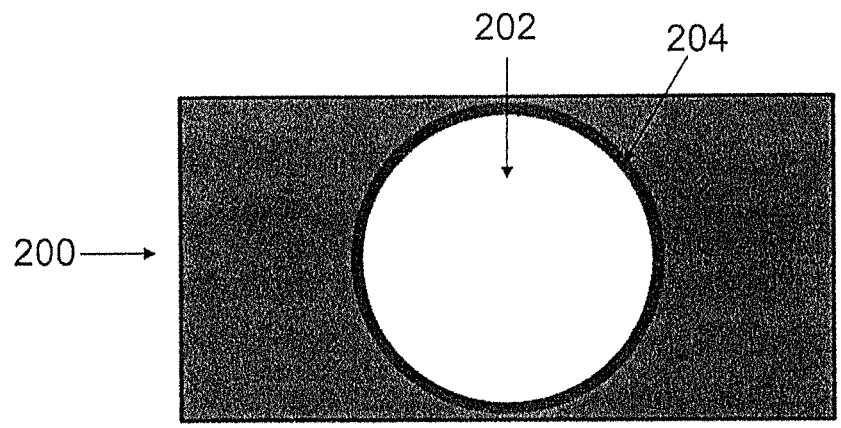
FIGS. 2A to 2D show an example of a film layer suitable for an over-pressurization relief device.

FIGS. 2A to 2D show an example of a film layer suitable for an over-pressurization relief device. FIG. 2A shows a front view of a film layer 202. The film layer materials may include but are not limited to Polyethylene, Polyamide, Polypropylene, Ethyl Vinyl Alcohol (EVOH), Polyethylene terephthalate (PET), Ethylene Vinyl Acetate Copolymer (EVAM), Linear Low Density Polyethylene (LLDPE), and/or Ultra Low Density Polyethylene (ULDPE). Burst pressure of the film layer 202 may be tested and qualified on a lot-to-lot basis.

In an example, the film layer 202 may be held into place by a frame 200 and be secured to the frame 200 using a sealing mechanism 204. The sealing mechanism 204 may include but is not limited to a mechanical sealing mechanism (such as a plate and frame holder), a heat sealing mechanism which thermally welds the film layer 202 into place, an ultrasonic welding mechanism, a radio frequency welding mechanism, a three dimensional printer, a vacuum forming unit, a chemical securing mechanism, a bonding mechanism (such as with adhesives), an electrostatic mechanism, and/or some other attachment or welding mechanism to hold the film layer 202 in place on the frame 200. The frame 200 may be, in an example, positioned at the external container 118. In another example, the film layer 202 may be held into place directly by the enclosure 100, e.g. by being sealed into the enclosure, or be held into place by the external container 118, e.g. by being attached directly to the external container. In other words, the frame 200 is optional.

Figure 2B:
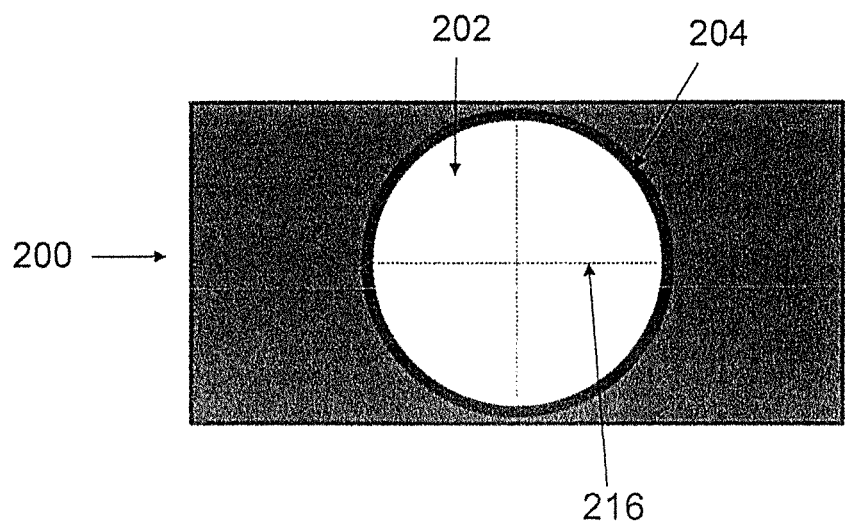

In an example, mechanical stretching of the film layer 202 may be employed prior to sealing to the frame 200 to weaken the film layer utilized and set a desired breakage pressure. In another example, the film layer 202 may undergo further processing to weaken the film structure. FIG. 2B shows a front view of the film layer 202 comprising perforations 216 exemplarily along the length of the film layer 202. These perforations 216 may be induced by means of a mechanical perforation wheel, die and punch perforations, heat treatment perforation, hot needle perforation, and/or laser perforation. The perforations 216 may allow the film layer 202 to tear along an axis at a specified pressure to reduce lot-to-lot variation of strength with the film types. The size, depth, and patterns of the perforations may be altered to break at a specific pressure range with a predetermined level of consistency. The perforations do not need to break through to the other side of the film layer 202. In an example, micro-punctures may be utilized on the film layer 202. In this example, a sterilizing grade filter may be utilized downstream of the film layer 202 to ensure that the sterility of the single-use container 10 is maintained during processing.

Figure 2C:
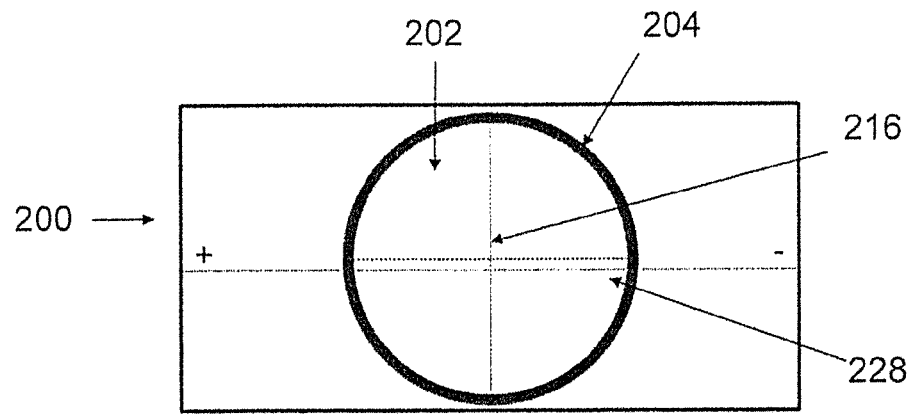
Figure 2D:
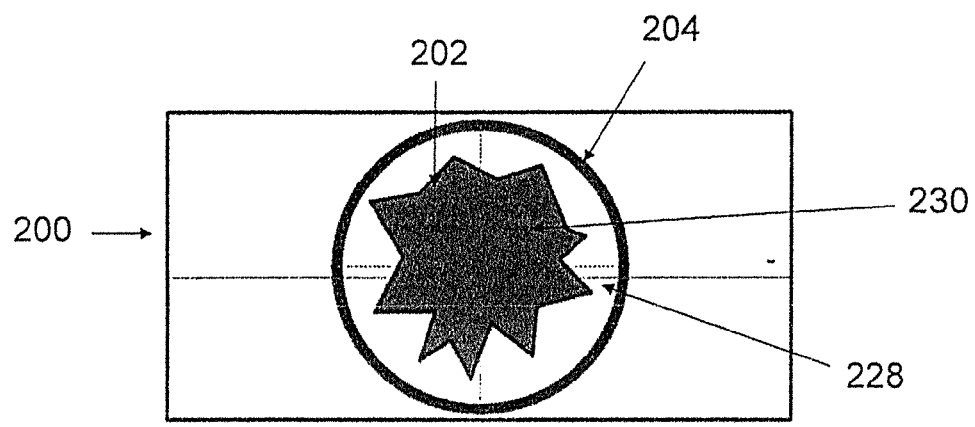

FIG. 2C shows a front view of the film layer 202 comprising an indicator of film failure. In an example, a thin electrical wire 228 may be positioned onto the film layer 202, extending across one of the surfaces of the film layer so as to connect two different points on the edge of the film layer by passing through a central region of the film layer 202. In another example, an extruded filament or some other means that can carry a small electric current across the film layer 202 may be utilized. The thin electrical wire 228 may function as a detector for the integrity of the film layer 202. When the pressure is lower than the breakage pressure, the thin electrical wire 228 may conduct an electric current across one surface of the film layer 202. FIG. 2D shows a front view of the film layer 202 after being exposed to the breakage pressure. The film layer 202 is configured to break when the enclosure 100 reaches the specified relief pressure to which the breakage pressure corresponds and a gap 230 may form inside the film layer 202. The gap 230 in the film layer 202 may breach the thin electrical wire 228, interrupting the conduction of electric current. In an example, the absence of current may be detected by a current sensor and a signal that the film layer 202 was breached may be consequently triggered. The signal may notify e.g. an operator of the breach, so that the operator may take appropriate measures such as replacing the film layer 202 and/or stopping the introduction of fluid into the enclosure 100.

In another example, a laser beam and/or a beam of light (not shown) may function as a detector for the integrity of the film layer 202. The laser beam may be positioned directly next to one face of the film layer 202 while a sensor may be positioned close to the other face, so that the film layer 202 is situated between the laser beam and the sensor. When the pressure is lower than the breakage pressure, the laser beam is detected by the sensor on the opposite side of the film layer 202. When the film layer 202 breaks due to being exposed to the breakage pressure, the breach in the film layer 202 may deflect the laser beam. The deflected laser beam does not reach the sensor on the other side of the film layer 202. Exemplarily, when the sensor fails to detect the laser beam, it may trigger a signal that the film layer 202 was breached. The signal may notify e.g. an operator of the breach so that the operator may take appropriate measures such as replacing the film layer and/or stopping the introduction of fluid into the enclosure.

Items other than a film layer may function as a conditional barrier element suitable for the over-pressurization device 120. In an example, a membrane filter may be used. Membrane filters are films (e.g. made of polymers) containing pores. Membrane filters may be exemplarily wetted with a fluid (wetting fluid), i.e. a fluid capable of maintaining contact with the solid surface represented by the edges of the pores. A wetted membrane filter may then constitute a barrier due to the adhesive forces between the wetting fluid and the structure of the membrane filter film (e.g. surface tension of a liquid). However if a pressure acting on the membrane filter is high enough to force the wetting fluid out of the pores, a bulk flow through the membrane filter can be achieved, i.e. a fluid with such a pressure may pass through the pores of the membrane filter. This pressure is called bubble point pressure and is determined, among others, by the size of the pores (for example between about 0.1 micrometers and about 10 micrometers), the material composing the membrane filter (for example plastic) and the nature of the wetting fluid (for example water and/or alcohol). The membrane filter may consist of a single layer of membrane or a multi-layered membrane (pre-filter and final filter layers).

Exemplarily, a membrane filter with a bubble point pressure corresponding to the specified relief pressure may be used as an over-pressurization device 120. In an example, the bubble point pressure may coincide with the specified relief pressure. In another example, there may be means between the enclosure 100 and the over-pressurization relief device 120 to alter the specified relief pressure so that the bubble point pressure may be different from the specified relief pressure.

The status of the membrane filter may be monitored by means of a sensor configured to trigger a signal when the membrane filter reaches a state of bulk flow. Exemplarily, this signal may be a visual and/or an auditory alarm and/or any other indication method that may notify e.g. an operator of the event. The sensor may be, but is not limited to, a pressure gauge, an indicator pressure gauge, a flow meter, a fluid sensor, and/or a pressure sensor.

Figure 3:
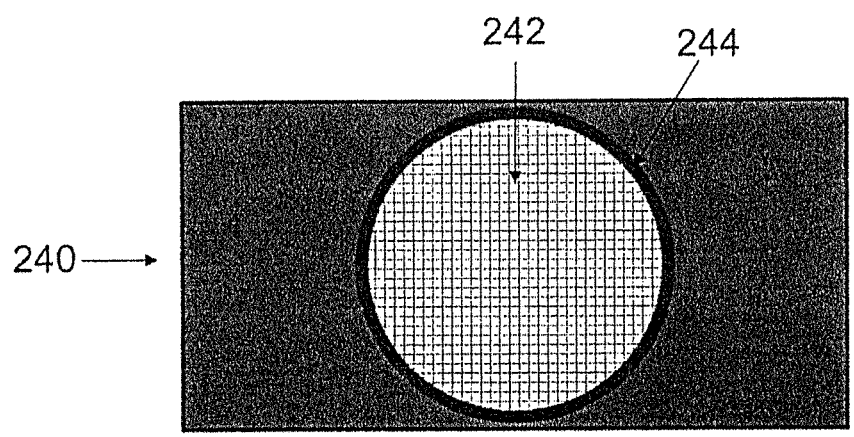
FIG. 3 shows an example of a membrane filter suitable for an over-pressurization relief device.
Figure 4A:
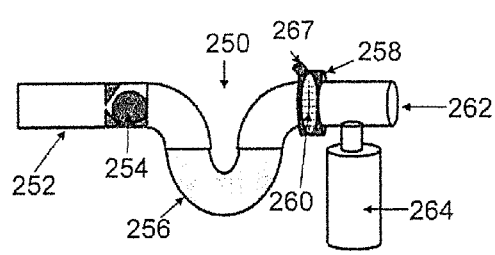
FIGS. 4A-4D show an example of an over-pressurization relief device comprising a membrane filter.
Figure 4B:
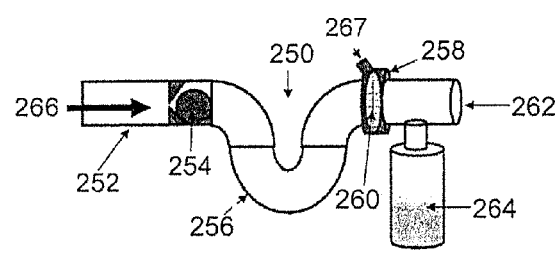
Figure 4C:
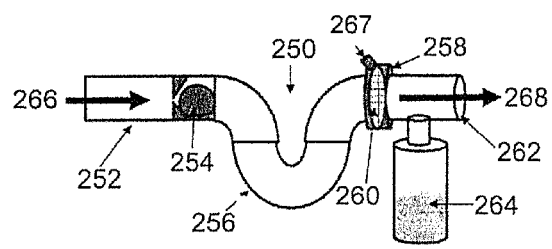
Figure 4D:
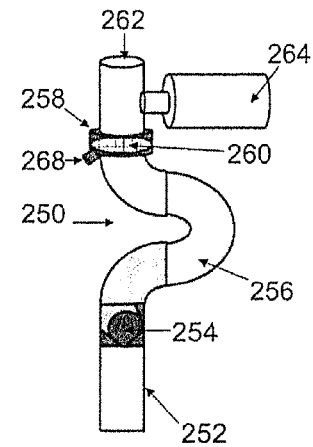
Figure 5A:
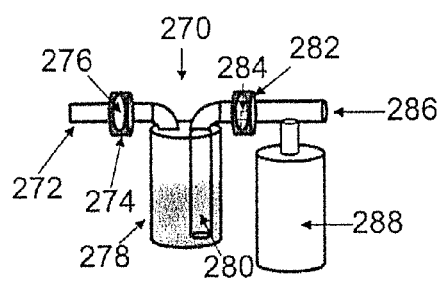
FIGS. 5A-5D show an example of a hybrid over-pressurization relief device comprising a film layer and a membrane filter.
Figure 5B:
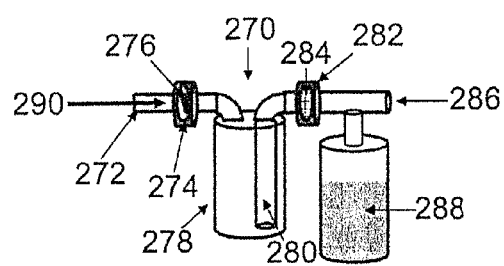
Figure 5C:
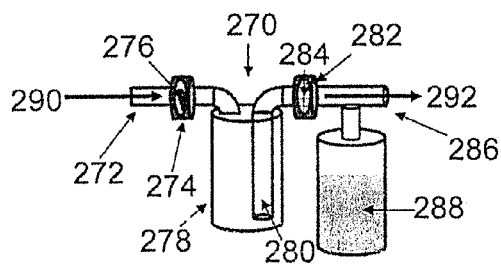
Figure 5D:
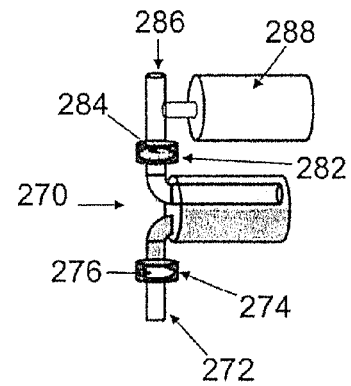

FIG. 3 shows an example of a membrane filter suitable for an over-pressurization relief device. The materials for the membrane filter 242 may include but are not limited to Polyethersulfone (PES), Polyamide (Nylon), Polypropylene (PP), Cellulose Acetate (CA), Polytetrafluoroethylene (PTFE) and/or Polyvinylidene fluoride (PVDF).

In an example, membrane filter 242 (front view) may be held by a frame 240 and secured to the frame using a sealing mechanism 244. The sealing mechanism 244 may include but is not limited to a mechanical sealing mechanism (such as a plate and frame holder), a heat sealing mechanism that thermally welds the membrane into place, an ultrasonic welding mechanism, a radio frequency welding mechanism, a three dimensional printer, a vacuum forming unit, a chemical securing mechanism, a bonding mechanism (such as with adhesives), an electrostatic mechanism, and/or some other attachment or welding mechanism to hold the membrane filter 242 in place on the frame 240. The frame 240 may be, in an example, positioned at the external container 118. In another example, the membrane filter 242 may be held into place directly by the enclosure 100, e.g. by being sealed into the enclosure, or be held into place by the external container 118, e.g. by being attached directly to the external container. In other words, the frame 240 is optional.

Exemplarily, the membrane filter 242 may be wetted with a wetting fluid (e.g. glycerol with water mixture). In one example, the membrane filter 242 may be wetted prior to installation of the single-use container 10 or prior to starting to introduce the fluid into the enclosure 100. In one example, a reservoir of wetting fluid may be prepositioned on the path of the fluid between the enclosure 100 and the membrane filter 242, as illustrated with reference to FIG. 4 below. The reservoir of wetting fluid may be e.g. a warm container that releases vapor and/or moisture to wet the membrane filter. The membrane filter 242 may also be wetted by a condensate of the fluid from the enclosure 100.

FIG. 4 shows an example of an over-pressurization relief device comprising a membrane filter 258. The membrane filter 260 constituting the over-pressurization relief device 120 may be part of a relief assembly 250 that may exemplarily be connected to the enclosure 100 by means of the aseptic connection 112 similarly to the relief assembly 110 of FIG. 1.

FIG. 4 view 'A' is a front view of an example of the relief assembly 250 comprising a tube length 252. The tube length 252 may be connected to a fluid backflow prevention device 254. A container and/or a 'U' bend 256 in the relief assembly piping may contain the wetting fluid for wetting the membrane filter 260. The membrane filter 260 may be sealed in a membrane holder 258 that is connected to a 'T' outlet 262. The 'T' outlet 262 may contain a wetting fluid collection container 264.

FIG. 4 views 'B' and 'C' show the relief assembly 250 after the enclosure 100 has reached the specified relief pressure. A pressure source 266 from the enclosure 100 may enter the tube length 252 and pass through the fluid backflow prevention device 254. The pressure source 266 may exemplarily cause the wetting fluid from the container and/or 'U' bend 256 in the relief assembly piping to push through the membrane filter 260 fully wetting it out. Afterwards, the wetting fluid may be led through the 'T' outlet 262 and then emptied into the wetting fluid collection container 264. In another example, the wetting fluid may be added via a port 267, such as a septum or needle free port, located on the membrane holder 258. After having wetted the membrane filter 260, the pressure source 266 may cause the wetted membrane filter 260 to bubble point. Bulk flow 268 of the fluid contained in the enclosure 100 may be achieved. The fluid may pass through the membrane filter 260 into the 'T' outlet 262 and then may be directed down a controlled pathway away from the single-use container 10 and from e.g. an operator.

FIG. 4 view 'D' shows an exemplary method to bring the wetting fluid back into the container and/or 'U' bend 256. The relief assembly 250 may be tilted by 90 degrees to the left and the wetting fluid may move from the wetting fluid collection container 264 to the fluid backflow prevention device 254, which prevents the wetting fluid from draining into the enclosure 100. Subsequently, the relief assembly 250 may be brought back to a horizontal position in order to restore the wetting fluid to its original position into the container and/or 'U' bend 256. The backflow prevention device 254 may additionally prevent the wetting fluid from entering into the enclosure 100 if the relief assembly 250 and tubing are e.g. oriented vertically, as shown in view D, when connected to the enclosure 100.

FIGS. 2A-2D and FIG. 3 show two examples of an over-pressurization relief device 120, comprising a film layer 202 and a membrane filter 242 respectively. It should be understood that the over-pressurization relief device 120 may comprise more than one film layer and more than one membrane filter. Exemplarily, the over-pressurization relief device 120 may be a hybrid comprising both a film layer and a membrane filter according to the above examples. In an example, the breakage pressure, the bubble point pressure and the specified relief pressure may coincide. In another example, means may be used to make the three pressures differ from each other.

FIG. 5 shows an example of a hybrid over-pressurization relief device comprising a film layer and a membrane filter. The film layer 276 and the membrane filter 284 constituting the over-pressurization relief device 120 may be part of a relief assembly 270 that may exemplarily be connected to the enclosure 100 by means of the aseptic connection 112 similarly to the relief assembly 110 of FIG. 1.

FIG. 5 view 'A' is a front view of an example of the relief assembly 270 comprising a tube length 272. The tube length 272 may be connected to a single-use film rupture disc holder 274 containing the film layer 276. A container 278 in the relief assembly piping may contain the wetting fluid for wetting the membrane filter 284. Under pressure the wetting fluid is exemplarily configured to rise through a dip tube 280 in the wetting fluid container 278 and fully wet out the membrane filter 284, which is sealed in a membrane holder 282. The membrane holder 282 may be connected to a 'T' outlet 286 that leads to a wetting fluid collection container 288.

FIG. 5 views 'B' and 'C' show an example of the relief assembly 270 after the enclosure 100 has reached the specified relief pressure. A pressure source 290 from the enclosure 100 may enter the tube length 272 and break the film layer 276 inside the single-use film rupture disc holder 274. The pressure source 290 may cause the wetting fluid from the container 278 to rise up under pressure through a dip tube 280 and fully wet out the membrane filter 284. The wetting fluid may then be pushed through the membrane filter 284 and into the 'T' outlet 262, where it drains into the wetting fluid collection container 288. The pressure source 290 may then cause the wetted membrane filter 284 to bubble point. Bulk flow 292 of the fluid contained in the enclosure 100 may be achieved. The fluid may pass through the membrane filter 284 into the 'T' outlet 286 and then may be directed down a controlled pathway away from the single-use container 10 and from e.g. an operator.

FIG. 5 view 'D' shows an exemplary method to bring the wetting fluid back into the container 278. The film layer 276 previously breached may be substituted with a new film layer 276, which may be e.g. loaded into the disc holder 274 by positioning a new frame 200 as the one shown in FIGS. 2A-2D. The relief assembly 270 may be tilted by 90 degrees to the left and the wetting fluid may move from the wetting fluid collection container 288 to the new film layer 276, which prevents the wetting fluid from draining into the enclosure 100. Subsequently, the relief assembly 270 may be brought back to a horizontal position in order to restore the wetting fluid to its original position into the container 278. The film layer 276 may additionally prevent the wetting fluid from entering into the enclosure 100 if the relief assembly 270 and tubing are e.g. oriented vertically, as shown in view D, when connected to the enclosure 100.

Figures 6A, 6B:
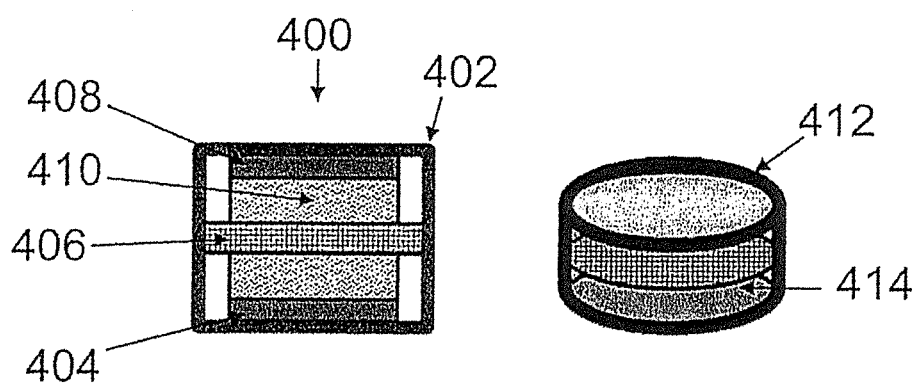
FIGS. 6A-B shows examples of a hybrid over-pressurization relief device comprising an internal film layer, a membrane filter, and an external film layer.

Exemplarily, the over-pressurization relief device 120 may be composed of multiple layers comprising an internal film layer in proximity to the enclosure 100, a membrane filter, and an external film layer, wherein the film layers and the membrane filter may be configured according to the above examples. FIGS. 6A-B shows an example of a multi-layered over-pressurization relief device.

A multi-layered over-pressurization relief device 400 may comprise a holder 402, an internal film layer 404, a membrane filter 406, and an external film layer 408. The multi-layered assembly may be filled with a wetting fluid 410 for the membrane filter 406, wherein the fluid is contained by the holder 402, the internal film layer 404, and the external film layer 408. The film layers 402 and 408 may include a moisture barrier to maintain the wetting fluid within the assembly. Exemplarily, the film layers 402 and 408 may be configured to break at a breakage pressure corresponding to the specified (predetermined or predeterminable) relief pressure and the membrane filter 406 may have a bubble point pressure corresponding to the specified relief pressure. When the enclosure 100 reaches the specified relief pressure, the internal film layer 402 may be at least partly breached and may consequently let the fluid from the enclosure 100 pass through the membrane filter 406, which has been fully wetted by immersion in the wetting fluid 410. When the bubble point of the membrane filter 406 is reached, the membrane filter 406 may achieve bulk flow and breach the exterior film layer 406, thereby relieving pressure from the enclosure 100. In an example, the external film layer 408 may include a chromic film that changes color when it undergoes mechanical stress, e.g. when it is stretched or punctured. In another example, the wetting fluid 410 may additionally contain an indicator dye that stains or colors the external film layer 408 to indicate clearly e.g. to the operator and/or a sensing device that the external film layer 408 was broken and that the specified relief pressure was reached within the enclosure 100. The multi-layered over-pressurization relief device 400 of FIG. 6A may, for example, be adapted as shown in FIG. 6B and used as a self-contained pressure relief device 412, filled with wetting fluid 414, on small single-use enclosures 100 such as any one of filter capsules, bottles, and containers.

FIG. 7 shows an example of a system comprising of a variable over-pressurization device where the film layer and/or the membrane filter may be changed to alter the pressure level at which the over-pressurization relief device is compromised. An exemplary usage of such a device is for pressure testing for leaks or integrity multiple single-use enclosures 100 which have different over-pressurization pressures or relief pressures such as with multiple filter capsules or multiple bag types having different maximum pressures or relief pressures such as with a Sartocheck® filter integrity testing or bag leak testing units.

Figure 7A:
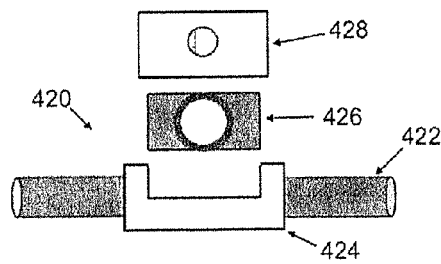
FIGS. 7A-7F shows an example of a variable over-pressurization relief device comprising a changeable frame.

FIG. 7A shows an exemplary method of a variable over-pressurization relief device 420 where a frame 426 containing a film layer and/or a membrane filter may be loaded into a holder 424. The holder 424 may be connected to a length of tubing 422 or other connection device which may be attached to a single exchangeable enclosure 100 at a time or is attached to multiple enclosures 100 simultaneously e.g. utilizing a manifold. The frame 426 may be secured into place with at least one cover component 428 which secures the frame 426 to place to the holder 424. The cover component 428 may contain an opening to a controlled pathway 500 to relieve the pressure in a controlled manner and/or may contain a filter to prevent aerosols from escaping to the environment during an over-pressurization event. The frame 426 containing a film layer and/or membrane filter with a specific relief pressure rating may be matched or connected to a single-use enclosure which has a comparable maximum enclosure 100 pressure rating and secured into place within the holder 424. The frame 426 particularly may be removed and replaced with another frame containing the same relief pressure rating (e.g. if the previous film in the frame failed or an over-pressurization event occurred) or a different relief pressure rating depending on what is required. The frame 426 may be sterilized in place within the holder 424 or may come pre-sterilized and connected to the holder utilizing an aseptic connection (not shown).

Figure 7B:
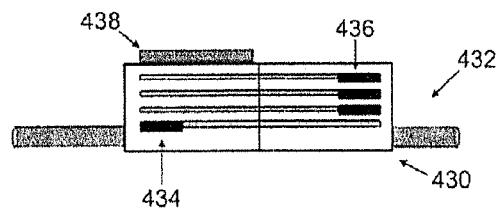

FIG. 7B shows an exemplary method of a variable over-pressurization relief device where plural frames exhibiting different relief pressure ratings (i.e. having different relief pressures) are internal to or arranged within a holder 430 and may be selected for use e.g. by means of operating external levers. Accordingly, by operating a selected external lever a deployed frame 434 is arranged within the flow path in fluid-connection with a tubing 432 while non-deployed frames 436 are left in the enclosure within the holder 430 separated from the flow path. Accordingly, it is possible to selectively adjust a specific relief pressure for the over-pressurization relief device, the selected specific relief pressure being selected from the plurality of different relief pressures of the plural frames. A cover component 438 may contain an opening to a controlled pathway 500 to relieve the pressure and/or may contain a filter to prevent aerosols from entering into the environment during an over-pressurization event. The frame containing at least one film layer and/or at least one membrane filter with a specific relief pressure rating may be matched to a single-use enclosure 100 which has a comparable maximum enclosure 100 pressure rating and the external lever for that particular pressure relief rating may be operated to arrange the respective frame in connection with the flow path while the other frames may be left in (e.g. pushed back or displaced into) the enclosure for non-deployed frames. Multiple frames may be deployed simultaneously or frames with the same pressure relief rating may be deployed if the previous film layer or membrane filter failed due to an over-pressurization event. The frames may be sterilized in place within the holder 430 or may come pre-sterilized and connected to the holder 430 e.g. utilizing an aseptic connection (not shown).

Figure 7C:
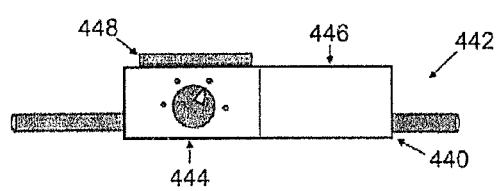

FIG. 7C shows another embodiment of a variable over-pressurization relief device 442 where the control device for selecting the frames substantially may be in the form of a selection dial 444 on a holder 440 instead of the external levers from View 'B'. The frames containing different relief pressure ratings are internal to the holder 440 and may be selected for use by utilizing the selection dial 444 to select the relief pressure rating of the frame the operator needs to deploy. The selection dial 444 may be arranged rotatable around an axis and/or may utilize an internal mechanism to move the frames into position. A cover component 448 may contain an opening to a controlled pathway 500 to relieve the pressure and/or may contain a filter to prevent aerosols from entering into the environment during an over-pressurization event. The frames may be sterilized in place within the holder 430 or may come pre-sterilized and connected to the holder e.g. utilizing an aseptic connection (not shown).

Figure 7D:
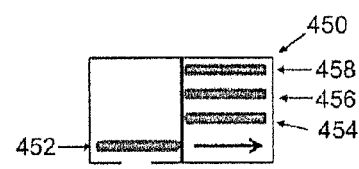

FIG. 7D shows an embodiment of the positioning of the internal frames of the variable over-pressurization relief devices 432 and 442 from FIGS. 7B and 7C. In this embodiment the frames are contained within a holder 450 where a frame 452 containing a film layer and/or membrane filter is within (or fluidically connected to) the flow path of the enclosure 100. Other non-deployed frames 454, 456, and 458 are arranged or left in the enclosure within the holder 450 separated from the flow path.

Figure 7E:
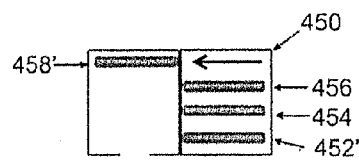

FIG. 7E shows an embodiment of the positioning of the internal frames of the variable over-pressurization relief devices 432 and 442 from FIGS. 7B and 7C. In this embodiment a frame 452' is returned to an area for non-deployed frames in the enclosure separated by the flow path while a frame 458' is moved into the deployed position within or connected to the flow path. The frames 452 through 458 may contain film layer and/or membrane filters that have a respective pressure relief rating which are the same or different from one another such as being positioned by increasing increments of pressure relief ratings of the frames where the operator may select the comparable pressure rating for the enclosure 100.

Figure 7F:
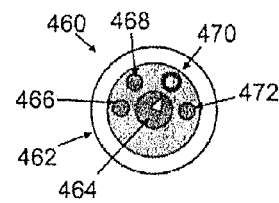

FIG. 7F shows an exemplary method of a variable over-pressurization relief device 460 where a holder 462 contains multiple film layers and/or membrane filters sealed to the holder 462 without using frames. A selection dial 464 may be utilized to select a film layer and/or membrane filter with a pressure relief rating comparable to or matching the pressure rating for the enclosure 100. The selection dial 464 may have an internal component that moves with the dial and/or covers all of the other film layers and/or membrane filters (or disconnects them) from the flow path with the exception of the one selected, which in this embodiment specifically is film layer 470 where film layers 466, 468, and 472 are covered or deactivated. The pathway above the selected film layer and/or membrane filter may contain a connection (not shown) to a controlled pathway 500 to relieve the pressure and/or may contain a filter to prevent aerosols from entering into the environment during an over-pressurization event. The sealed film layer(s) and/or membrane filter(s) may be sterilized in place within the holder 460 or may come pre-sterilized and connected to the holder utilizing an aseptic connection (not shown).

As mentioned with reference to FIGS. 1, 4 and 5, the over-pressurization relief device 120 may be connectable to a controlled pathway for relieving the fluid from the enclosure in a controlled manner. Therefore the over-pressurization relief device 120 may provide a safe way to discharge fluid in excess with respect to a desired pressure in the enclosure 100, e.g. the relief pressure. Exemplarily, the presence of a controlled pathway may provide a release channel for the fluid to travel through without releasing aerosols to the environment and/or an operator and without compromising the sterile setup of the single-use container 10.

Exemplarily, the controlled pathway may include at least one tubing length away from the single-use container 10. The controlled pathway may be sterilized prior to being connected to the single-use container 10.

In an example, one or more filters may be used in the controlled pathway downstream of the over-pressurization relief device 120 to prevent aerosolization of the enclosure contents. The filter may maintain the sterility of the single-use container 10 while pressure is being relieved.

In another example, the contents of the enclosure 100 may be directed to a drain and/or to a vented container to direct any potential aerosols away from e.g. an operator.

In yet another example, the controlled pathway may connect the single-use container 10 to an external pressure relief device.

Figure 8:
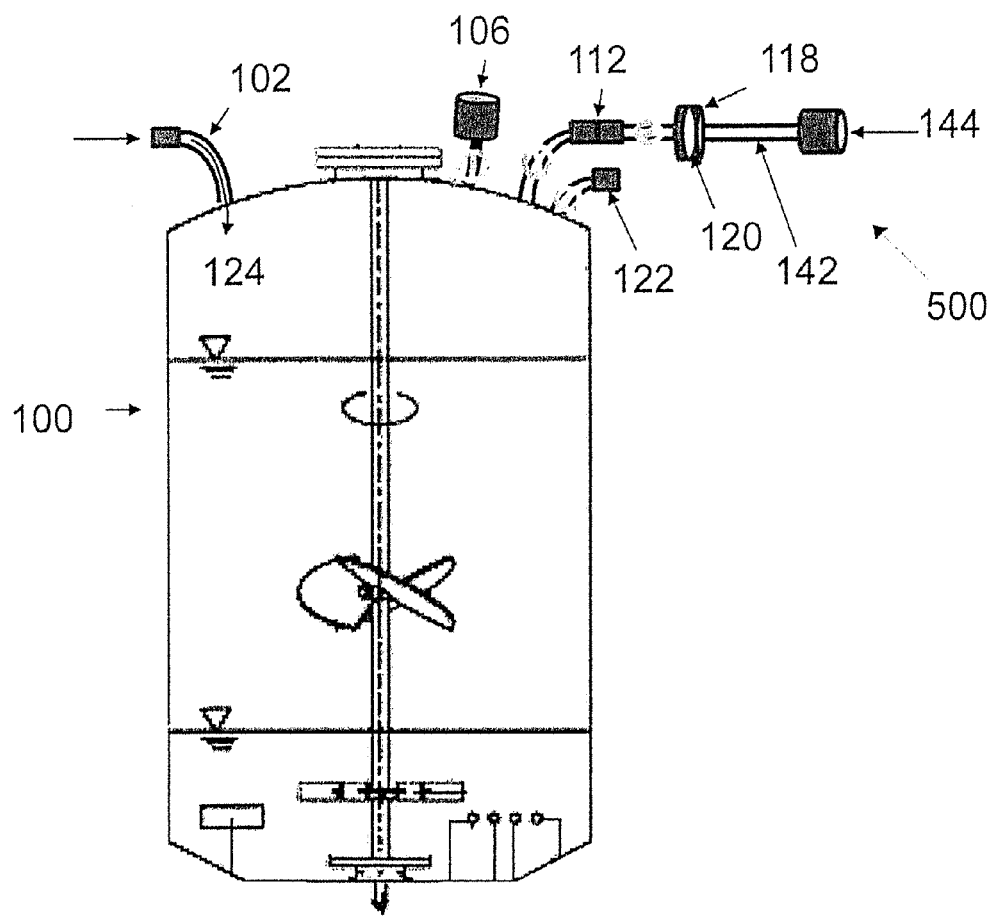
FIG. 8 shows an example of a system comprising a single-use container and a controlled pathway containing a filter.

FIG. 8 shows an example of a system comprising a single-use container and a controlled pathway containing a filter. In FIG. 8, elements identical to those shown in FIG. 1 are indicated by the same reference signs and detailed explanations thereof will not be provided.

A controlled pathway 500 is connected after the over-pressurization relief device 120. The controlled pathway may comprise a length of tubing 142 and at least one sized filter 144. The filter may be, but is not limited to, a hydrophobic vent filter, a hydrophilic liquid filter, a sterilizing grade filter, a virus retentive filter, a combination hydrophilic/hydrophobic filter, a barrier filter, a filter train containing multiple filters, and/or a branch of filters which could include separate hydrophilic and hydrophobic filters. Exemplarily, the at least one filter 144 is in place to prevent biohazardous aerosols coming from the enclosure 100 from reaching an operator and/or the work environment. The aerosols may be contained by the filter 144, maintaining the sterility of the single-use container 10.

In another example, the aerosols may be further directed e.g. by means of additional tubing lengths in the controlled pathway 500 to a specified location.

Figure 9:
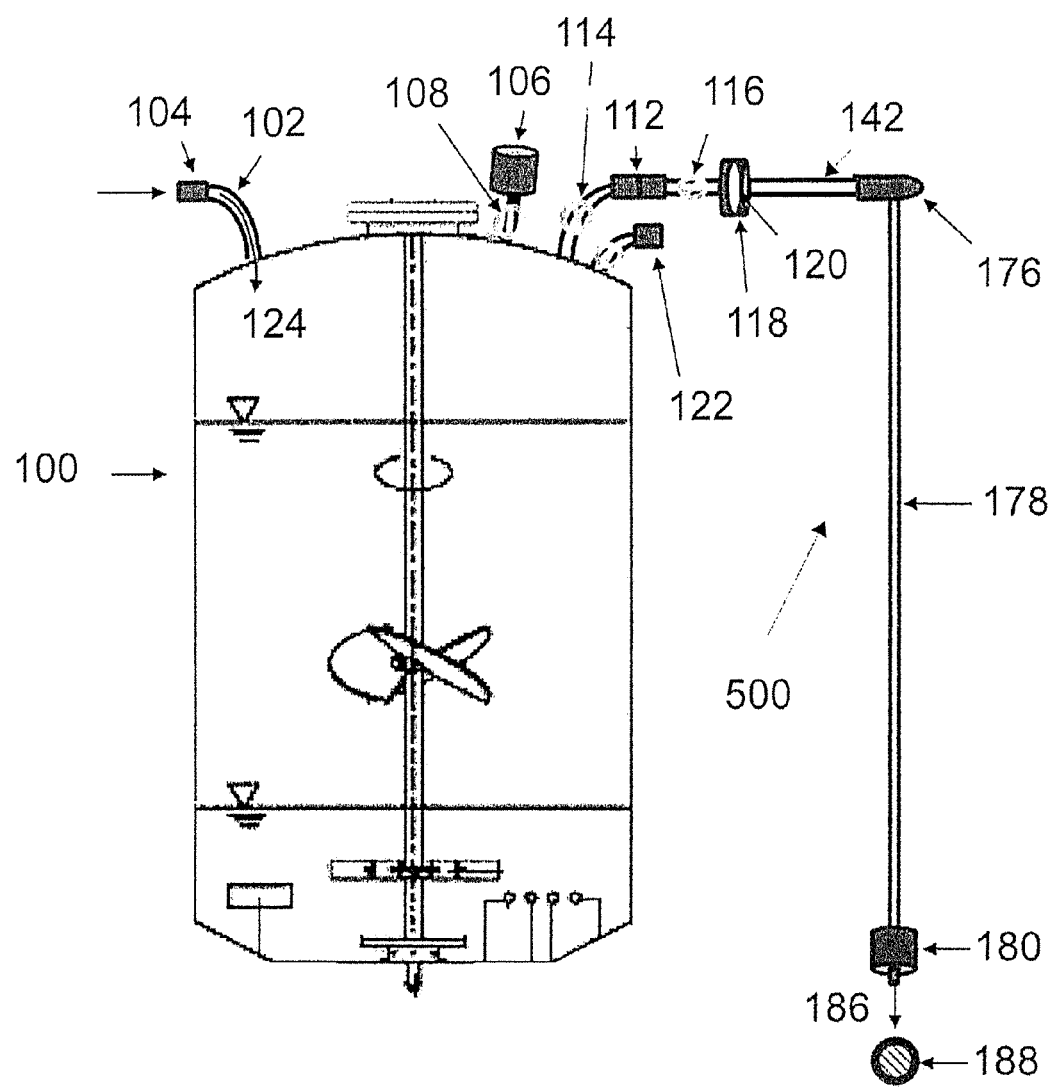
FIG. 9 shows an example of a system comprising a single-use container and a controlled pathway containing a connection to a specified location.

FIG. 9 shows an example of a system comprising a single-use container and a controlled pathway containing a connection to a specified location. In FIG. 9, elements identical to those shown in FIG. 1 are indicated by the same reference signs and detailed explanations thereof will not be provided.

A controlled pathway 500 is connected after the over-pressurization relief device 120. The controlled pathway may comprise a length of tubing 142 and an elbow connection (not shown) that may direct the fluid path to another length of tubing 178. In an example, a pressure relief valve 176 may be provided on the path, so that the fluid from the enclosure 100 may be directed to the length of tubing 178 once it has reaches a specified pressure. In another example, the pressure relief valve 176 may vent to the work environment in a controlled space, such as under an isolation hood (not shown) with venting for aerosols.

In an example, the length of tubing 178 may direct the fluid from the enclosure 100 to a filter 180, a controlled drain 188, and/or a vented container (not shown). The filter 180 may be, but is not limited to, a hydrophobic vent filter, a hydrophilic liquid filter, a sterilizing grade filter, a virus retentive filter, a combination hydrophilic/hydrophobic filter, a barrier filter, a filter train containing multiple filters, and/or a branch of filters which could include separate hydrophilic and hydrophobic filters. The filter 180 is in place to prevent biohazardous aerosols coming from the enclosure 100 from reaching an operator and/or the work environment.

Figure 10A:
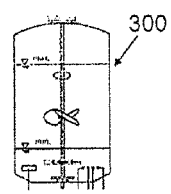
FIGS. 10A-10Q shows examples of different enclosures for single-use containers.
Figure 10B:
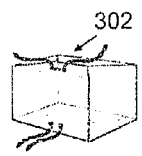
Figure 10C:
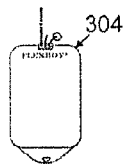
Figure 10D:
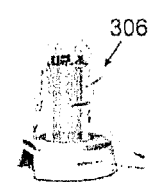
Figure 10E:
Figure 10F:
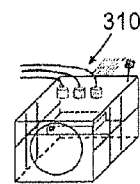
Figure 10G:
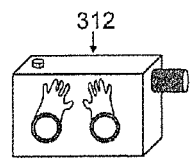
Figure 10H:
Figure 10I:
Figure 10J:
Figure 10K:
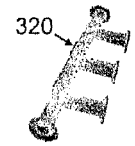
Figure 10L:
Figure 10M:
Figure 10N:
Figure 10O:
Figure 10P:
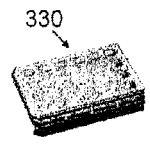
Figure 10Q:
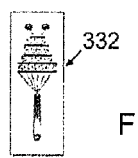

Exemplarily, a single-use container as shown in FIG. 1 may comprise different types of enclosure to which an over-pressurization relief device may be fluidly connected. FIGS. 10A-10Q show examples of different enclosures for single-use containers.

Enclosure 300 (FIG. 10A) is a single-use flexible walled bioreactor bag (front view), such as a Biostat® Cultibag® Stirred Tank Reactor (STR) bioreactor bag, a Wave® type Cultibag® RM rocking bioreactor bag, a shaking ORB® type bioreactor bag or other flexible bioreactor bag types. Enclosure 302 (FIG. 10B) is a single-use 3D bioprocessing bag (corner view), such as a Palletank® type storage or mixing bag, a LevMix® or MagMix® mixing bag, other flexible 3D Bioprocessing bags, or 3D bag enclosures. Enclosure 304 (FIG. 10C) is a single-use 2D bioprocessing bag (front view), such as a FlexBoy®, Celsius®, or other 2D Bioprocessing bag types. Enclosure 306 (FIG. 10D) is a single-use rigid walled bioreactor container (front view), such as the Biostat® SU, the TAP Biosystems ambr15, the ambr250, and other rigid walled bioreactor containers. Enclosure 308 (FIG. 10E) is a single-use rigid walled CellSTACK® container (front view), which is a multi-chamber rigid walled plastic container. It is utilized for tissue culture of growing adherent cells such as 1 chamber, 5 chambers, 10 chambers, 40 chambers, etc. . . . and other rigid walled CellSTACK® containers. Enclosure 310 (FIG. 10F) is a single-use three-dimensional printer that contains pneumatically inflated bags to position the gantry. In this example, both the enclosure of the single-use three-dimensional printer and the individual pneumatically inflated bags may contain an over-pressurization relief device. Enclosure 312 (FIG. 10G) is a single-use isolator chamber or glove box where the over-pressurization relief device may be located on the chamber body itself, the gloves, or the frames to hold the gloves in place. Enclosure 314 (FIG. 10H) is a single-use filter capsule such as a MidiCap®, MaxiCap®, T-style MaxiCap®, which can utilize an over-pressurization relief device to prevent capsule failure and potential explosion of the capsule body in the event of an over-pressurization event. Enclosure 316 (FIG. 10I) is a single-use aseptic sampling device such as the TakeOne® sampler. In this example the over-pressurization relief device may be contained in the aseptic holder device, the tubing connection(s), and/or the sample holding bag(s). Enclosure 318 (FIG. 10J) is a single-use aseptic connector such as an OPTA® connector where the over-pressurization relief device may be contained in one connector (male, female, or genderless) or contained in both connectors. Enclosure 320 (FIG. 10K) is a single-use manifold that splits a fluid line into a plurality of connections. Enclosure 322 (FIG. 10L) is a single-use tubing length such as silicone tubing or thermoweldable tubing that contains an over-pressurization relief device to prevent the rupture of the tubing during an over-pressurization event. Enclosure 324 (FIG. 10M) is a single-use carboy container for the storage, holding and/or disposal of fluids where the bottle and/or the cap may contain an over-pressurization relief device. Enclosure 326 (FIG. 10N) is a single-use bottle where the bottle and/or the cap may contain an over-pressurization relief device. Enclosure 328 (FIG. 10O) particularly is a conical tube such as a Falcon® Tube which may contain the over-pressurization relief device in either the fluid enclosure body or in the cap. Enclosure 330 (FIG. 10P) particularly may be a single-use multiwell plate where the plate and/or the plate cover may contain an over-pressurization relief device. Enclosure 332 (FIG. 10Q) may be a single-use microfluidic container which may contain an over-pressurization relief device in the holder or within the subcomponents of the device itself such as a reservoir, a microfluidic fluid pathway, or the site of fluid injection into the microfluidic device. Accordingly, the over-pressurization relief device 120 comprises at least one of: (i) at least one internal film layer configured to break at a breakage pressure corresponding to the specified relief pressure, (ii) at least one membrane filter configured to have a bubble point pressure corresponding to the specified relief pressure, and (iii) at least one external film layer configured to break at a breakage pressure enclosed within a holder, wherein the internal and/or external film layers may hold or include a wetting fluid reservoir for the membrane filter.

What is claimed is:

1. A single-use container (10) comprising:
   an enclosure (100) for a fluid; and
   an over-pressurization relief device (120) fluidly connected to the enclosure (100), the over-pressurization relief device (120) being configured to relieve pressure from the enclosure (100) when a pressure of the fluid within the enclosure (100) exceeds a specified relief pressure, the specified relief pressure being set to be lower than the burst pressure of the enclosure (100), the over-pressurization relief device (120) being connectable to a controlled pathway for relieving the fluid from the enclosure (100) via the controlled pathway, and further comprising at least one membrane filter (242) configured to have a bubble point pressure corresponding to the specified relief pressure.

2. The single-use container (10) of claim 1, wherein the single-use container (10) is a sterilizable plastic disposable container that is adapted to contain at least one fluid.

3. The single-use container (10) of claim 1, wherein the over-pressurization relief device (120) is integrated into the enclosure (100).

4. The single-use container (10) of claim 3, wherein the over-pressurization relief device (120) is configured to be sterilized utilizing at least one validated method selected from the group consisting of gamma irradiation, autoclaving, steam sterilization and chemical sterilants.

5. The single-use container (10) of claim 1, wherein the over-pressurization relief device (120) is located at an external container (118) that is aseptically connected (112) to the enclosure (100).

6. The single-use container (10) of claim 5, wherein the over-pressurization relief device (120) is configured to be sterilized utilizing at least one validated method selected from the group consisting of gamma irradiation, autoclaving, steam sterilization and chemical sterilants.

7. The single-use container (10) of claim 1, wherein the over-pressurization relief device (120) comprises at least one film layer (202) configured to break when being exposed to a breakage pressure corresponding to the specified relief pressure.

8. The single-use container (10) of claim 7, wherein the film structure of the at least one film layer (202) is weakened in at least one position to set the breakage pressure.

9. The single-use container (10) of claim 8, wherein the film structure is weakened by at least one of stretching, perforation, chemical processing, and physical processing.

10. The single-use container (10) of claim 7, wherein the over-pressurization relief device (120) comprises multiple film layers and/or membrane filters having different pressure relief ratings which can be selected and deployed into a flow path of the enclosure (100) to adjust the specified relief pressure.

11. The single-use container (10) of claim 1, further comprising a reservoir of wetting fluid.

12. The single-use container (10) of claim 11, wherein the single-use container contains at least one of the following: a valve, a backflow prevention device, a film layer to prevent the wetting fluid in the fluid reservoir from entering into the enclosure (100).

13. The single-use container (10) of claim 1, further comprising at least one of a chiller and/or a coating on the membrane filter (242) configured to facilitate condensation onto the at least one membrane filter (242).

14. The single-use container (10) of claim 1, further comprising at least one sensor configured to indicate when the at least one membrane filter (242) has achieved bulk flow due to being exposed to the bubble point pressure.

15. The single-use container (10) of claim 1, wherein the over-pressurization relief device (120) comprises multiple film layers and/or membrane filters having different pressure relief ratings which can be selected and deployed into a flow path of the enclosure (100) to adjust the specified relief pressure.

16. The single-use container of claim 1, wherein the over-pressurization relief device (120) further comprises a pressure relief valve.

17. A system for the prevention of over-pressurization in a single-use container (10), the system comprising:
    the single-use container (10) of claim 1, and
    the controlled pathway (500) connected to the over-pressurization relief device (120) of the single-use container (10).

18. The system of claim 17, wherein the controlled pathway (500) connects to at least one of an external pressure relief device, an external filter (144; 180), and a drain (188).

19. The system of claim 17, wherein the controlled pathway (500) comprises at least one sterilizing-grade filter.

20. A single-use container (10), comprising:
    an enclosure (100) for a fluid;
    an over-pressurization relief device (120) fluidly connected to the enclosure (100) and being configured to relieve pressure from the enclosure (100) when a pressure of the fluid within the enclosure (100) exceeds a specified relief pressure that is set to be lower than the burst pressure of the enclosure (100), the over-pressurization relief device (120) being connectable to a controlled pathway for relieving the fluid from the enclosure (100) via the controlled pathway, and the over-pressurization relief device (120) having at least one film layer (202) configured to break when being exposed to a breakage pressure corresponding to the specified relief pressure; and
    at least one sensor configured to indicate when the at least one film layer (202) has been breached because exposed to the breakage pressure.

21. The single-use container (10) of claim 20, wherein the over-pressurization relief device (120) comprises at least one membrane filter (242) configured to have a bubble point pressure corresponding to the specified relief pressure.

22. The single-use container (10) of claim 20, wherein the at least one film layer configured to break at a breakage pressure corresponding to the specified relief pressure is an internal film layer.

23. The single-use container (10) of claim 20, wherein the at least one film layer configured to break at a breakage pressure corresponding to the specified relief pressure is at least one external film layer.

24. A single-use container (10), comprising:
an enclosure (100) for a fluid; and
an over-pressurization relief device (120) fluidly connected to the enclosure (100) and being configured to relieve pressure from the enclosure (100) when a pressure of the fluid within the enclosure (100) exceeds a specified relief pressure that is set to be lower than the burst pressure of the enclosure (100), the over-pressurization relief device (120) being connectable to a controlled pathway for relieving the fluid from the enclosure (100) via the controlled pathway, and the over-pressurization relief device (120) having at least one film layer (202) configured to break when being exposed to a breakage pressure corresponding to the specified relief pressure, wherein the at least one film layer (202) comprises an electrical wire (228) that carries an electric current, the electrical wire (228) being configured to break and to trigger an alarm when the at least one film layer (202) is exposed to the breakage pressure.

25. A single-use container (10), comprising:
an enclosure (100) for a fluid;
an over-pressurization relief device (120) fluidly connected to the enclosure (100) and being configured to relieve pressure from the enclosure (100) when a pressure of the fluid within the enclosure (100) exceeds a specified relief pressure that is set to be lower than the burst pressure of the enclosure (100), the over-pressurization relief device (120) being connectable to a controlled pathway for relieving the fluid from the enclosure (100) via the controlled pathway, and the over-pressurization relief device (120) having at least one film layer (202) configured to break when being exposed to a breakage pressure corresponding to the specified relief pressure; and
at least one of a laser and/or a beam of light adjacent the at least one film layer (202), wherein the at least one of a laser and/or a beam of light is configured to be deflected and to trigger an alarm when the at least one film layer (202) is exposed to the breakage pressure.

* * * * *